United States Patent [19]

Hinant et al.

[11] Patent Number: 5,168,761
[45] Date of Patent: Dec. 8, 1992

[54] AUTOMATED SPRING PACK TESTING METHOD

[75] Inventors: John G. Hinant; Harry Honig; Albert J. Servas, all of Lynchburg, Va.

[73] Assignee: B&W Nuclear Service Company, Lynchburg, Va.

[21] Appl. No.: 756,705

[22] Filed: Sep. 9, 1991

[51] Int. Cl.⁵ ............................................. F16B 31/02
[52] U.S. Cl. ....................................... 73/791; 73/161
[58] Field of Search ................................ 73/791, 161

[56] References Cited

U.S. PATENT DOCUMENTS

| | | | |
|---|---|---|---|
| 3,165,926 | 1/1965 | Orr et al. | 73/161 |
| 3,285,065 | 11/1966 | Ragen et al. | 73/161 |
| 4,157,033 | 6/1979 | Shereda et al. | 73/161 |
| 5,000,040 | 3/1991 | Charbonneau et al. | 73/168 |
| 5,088,333 | 2/1992 | Kiely et al. | 73/161 X |

FOREIGN PATENT DOCUMENTS 2062168  5/1981  United Kingdom ............... 73/161

Primary Examiner—Jerry W. Myracle
Attorney, Agent, or Firm—Robert J. Edwards; Michael L. Hoelter

[57] ABSTRACT

This invention pertains to an automated method of testing the spring pack found in motor operated valves. It includes the steps of compressing the spring pack in a test stand while the compressive load applied and the vertical displacement occurring as a result of such loading is measured. This data is sent to a computer that records selected load measurements which correspond to pre-selected displacement values. Afterwards, this data is reported such as by a graph or other report that provides a comparison of the pre-selected displacement values with its respective compressive load.

9 Claims, 10 Drawing Sheets

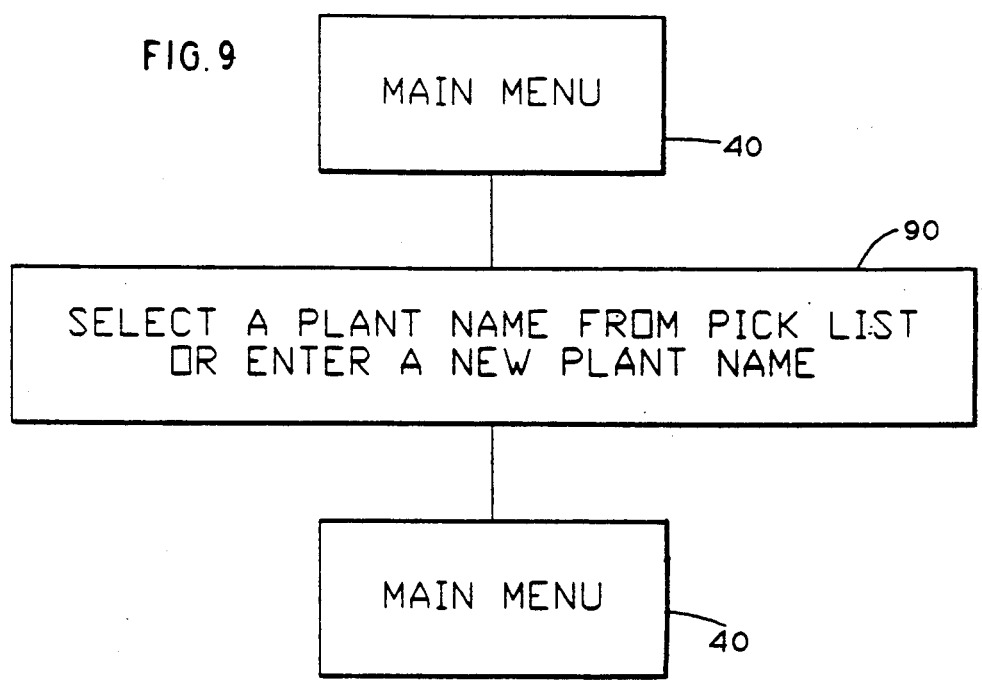
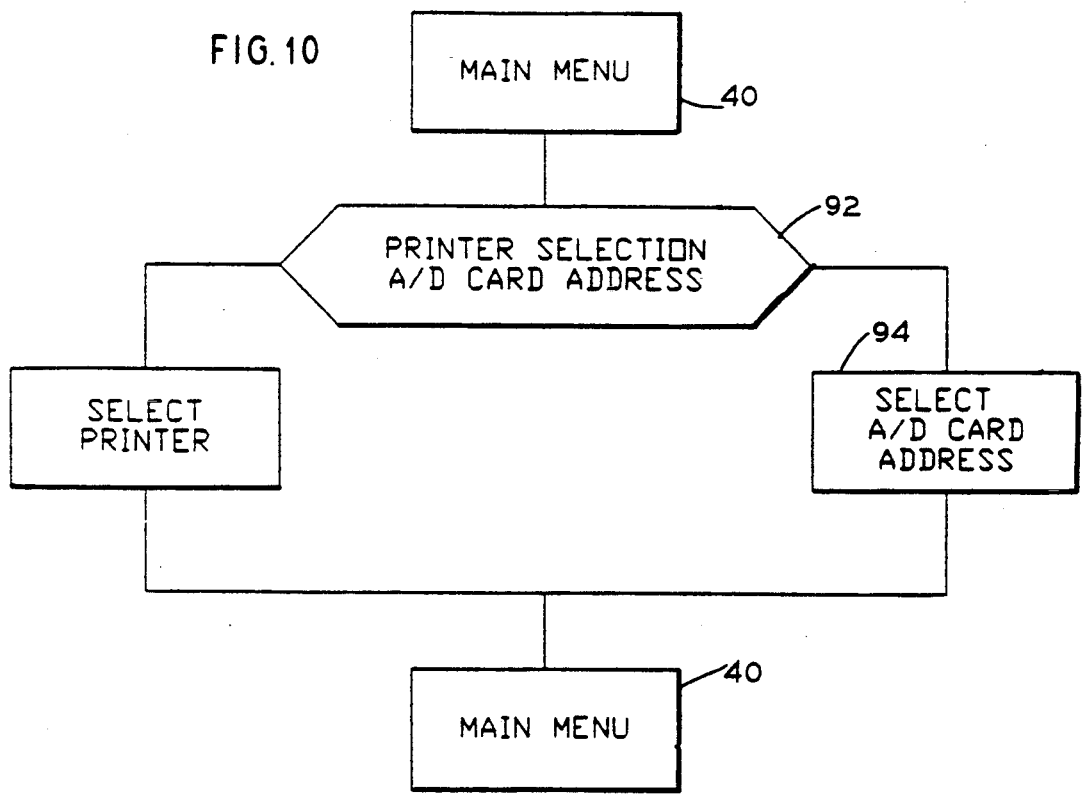

AUTOMATED SPRING PACK TESTING METHOD

FIELD OF THE INVENTION

This invention pertains to the testing of motor operated valves and more specifically, to the testing and analysis of a motor operated valve's spring pack to verify that the spring pack is functioning within acceptable specifications.

BACKGROUND OF THE INVENTION

Motor operated valves normally contain a spring pack which is biased whenever torque is applied to the valve shaft. A torque switch is coupled to the spring pack such that when a certain level of torque is reached, such as at the fully open or fully closed position of the valve shaft, the switch stops the motor and prevents it from applying any more torque.

As can be imagined, should the spring pack not conform to specifications by generating false or inaccurate measurements, the torque switch will be inappropriately triggered. If the switch is triggered too early, the valve may not be in its fully open or fully closed position thereby affecting flow through the valve. If the switch is triggered too late, the motor will be allowed to operate too long thereby possibly causing damage to the valve body or stem. Thus it is important for spring packs to accurately operate within their specified range.

In the past, two separate steps were required to test the spring packs for motor operated valves. The first step involved the compressing of the spring pack in a test stand. Generally, the test stand utilized a load cell and a LDT sensor that fed into a display box. At various times during the test, different compression readings were manually taken. The second step involved entering this recorded data into a computer so that a software program could graphically display the entered data. Afterwards, this data was evaluated and, depending upon the evaluation, the spring pack was either reinserted into the motor operated valve or it was discarded, there were no provisions for comparing the data just entered with any previous test data or standard.

It is thus an object of this invention to provide a method and apparatus for testing spring packs which is quicker, more accurate, and more efficient than any such system now known. Another object of this invention is to provide a system that automatically feeds (if such is desired) certain test data to a computer for analysis. Other embodiments permit the user to semi-automatically feed such data to the computer or this data can be manually entered. Still another object of this invention is to provide a spring pack test stand that is easy to use without the need to bolt or otherwise fasten the spring pack to the test stand. These and other objects will become obvious upon further investigation.

SUMMARY OF THE INVENTION

This invention pertains to the testing of a spring pack found in motor operated valves. It comprises the steps of compressing the spring pack in a test stand while simultaneously measuring the compressive load applied. At the same time, the vertical displacement of the spring pack is measured due to this compressive load. Both sets of measurements are sent to a computer which records the load measurement that corresponds to a pre-selected vertical displacement value. Finally, this selected information (compressive load value and vertical displacement) is reported such as through a graph.

BRIEF DESCRIPTION OF THE DRAWINGS

FIG. 9 is a partial flow diagram illustrating the Pick Another Plant component of the software program.

FIG. 10 is a partial flow diagram illustrating the Hardware Setup component of the software program.

DETAILED DESCRIPTION OF THE DRAWINGS

Figure 1:
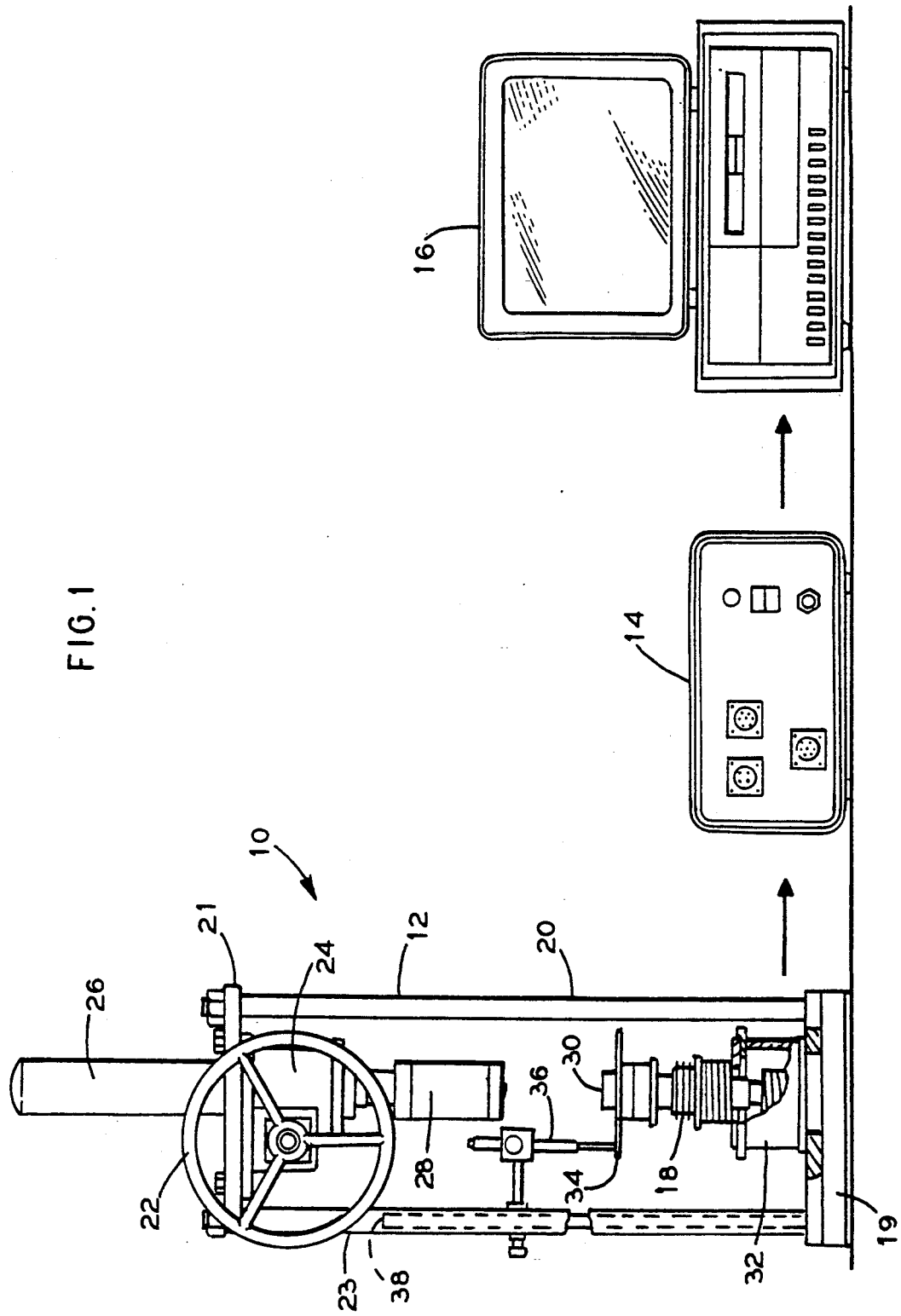
FIG. 1 is a pictorial view of the invention illustrating the spring pack test stand, the signal conditioning box, and the computer.

Referring initially to FIG. 1, there is shown testing assembly 10 which includes test stand 12 and its assorted hardware and sensors, signal conditioning box 14, and computer 16. During operation, spring pack 18 is inserted within stand 12 where certain measurements are made. The sensors making these measurements are controlled by signal conditioning box 14 which sends this data to computer 16 for subsequent compilation and analysis.

Test stand 12 incorporates rigid frame 20 having a base 19, top 21, and supports 23 therebetween. Frame 20 supports hand wheel 22 and machine screw jack 24. Machine screw jack 24 is configured to transform the rotary motion of hand wheel 22 into a vertical linear motion. It includes an elongated and possibly threaded shaft (not shown) that extends within housing 26. This shaft is moved vertically at will upon the rotation of hand wheel 22 so as to engage spring pack 18.

Secured to the end of this shaft is load cell 28 which both engages spring pack 18 and measures the compressive force applied to spring pack 18. By rotating hand wheel 22, load cell 28 is moved downward so as to engage spring pack 18. Further rotation of hand wheel 22 causes a compressive force to be applied to spring pack 18 via load cell 28. Basically, hand wheel 22 is manually operated to compress load cell 28 against spring pack 18 throughout the desired compressive range. The compressive force measured by load cell 28 is sent to signal conditioning box 14 for further use and analysis.

Prior to this operation, top cap assembly 30 is secured to spring pack 18 to protect it during compression. Top cap assembly 30 also secures spring pack 18 to test fixture base 32 so that a variety of differently sized spring packs can be measured. Additionally, each spring pack 18 is oriented on test fixture base 32 so that its shaft extends downward as the spring is compressed. With the orientation shown, there is no need to bolt or otherwise secure spring pack 18 to fixture base 32 since base 32 provides all the support needed. It should also be noted that base 32 is designed not to compress under loading so that accurate measurements of spring pack 18 can be taken.

To determine the vertical displacement of spring pack 18 during compression, reference plate 34 is secured to top cap assembly 30. Plate 34 serves as a horizontal reference plane during the compression of spring pack 18. With this configuration, as load cell 28 engages top cap assembly 30 and compresses spring pack 18 downward, reference plate 34 is likewise moved downward in direct relation to the compression of spring pack 18.

A linear variable differential transformer (or LVDT) 36 is used to engage reference plate 34 in order to measure the displacement of spring pack 18 during such loading. The total distance spring pack 18 is compressed, and any other desired intermediate measurement, is determined by LVDT 36 with this data being sent to signal conditioning box 14 for further use and analysis. LVDT 36 slides along post 38 so that it can be positioned relative to reference plate 34 and so that the anticipated range of displacement of spring pack 18 will fall within the measuring range of LVDT 36.

Both load cell 28 and LVDT 36 are wired to send their respective signals first to signal conditioning box 14 before such data is sent to computer 16. Signal conditioning box 14 consists of signal conditioning modules, connectors, appropriate wiring and circuitry to provide precise excitation voltages to load cell 28 and LVDT 36. Box 14 then sends the boosted output signals from these sensors to computer 16. It also displays this vertical displacement and compressive force data for use by the user should such be desired. As can be imagined, signal conditioning box 14 is energized after it is connected to test stand 12, a power supply, and computer 16.

Computer 16 contains the software and interface connections that allow the user to test spring pack 18 and to store spring pack test data, view and compare test data, analyze test data, or print test data as desired or needed. Computer 16 can also be provided with information relating to the motor operated valve whose spring pack 18 is being tested. Such information can include valve number, test date, operator type, operator manufacturer, shop order number, size of spring pack, serial number, spring pack number, valve stem diameter, number of threads per inch, number of starts, desired closing thrust, desired opening thrust, desired closing torque, desired opening torque, as-found open torque switch setting, as-found closed torque switch setting, and comments.

Once spring pack 18 is positioned within test stand 12, hand wheel 2 is rotated to begin the testing of spring pack 18. Such testing can be automatic, semi-automatic, or manual, as desired. In the automatic mode, computer 16 selects which points (compressive force and/or displacement distance) will be recorded. These points are generally based on those displacement distances which correlate to the motor operated valve's torque switch settings. In the semi-automatic mode, the user selects which data points will be stored. In the manual mode, the user not only selects which data points will be stored, but the user also manually inputs all such data, signal conditioning box 14 being bypassed.

After the data is fed computer 16, generally other additional data relating to the motor operated valve is inputted. This other additional data usually being the results obtained from tests performed on the valve's torque switch. All the data collected can be stored, analyzed, evaluated, edited, viewed graphically, compared with standards, compared with previous tests by overlaying graphics, or printed out both numerically or graphically.

Computer 16 can show if spring pack 18 is within acceptable tolerances, and thus remains useful, or whether a new torque switch setting is required to achieve acceptability.

A main advantage of test stand 12 is the ease with which spring pack 18 can be inserted. This is attributed to the direction in which spring pack 18 is compressed. When spring pack 18 is compressed, the shaft on spring pack 18 is allowed to extend into test fixture base 32. No disassembly of test stand 12 is required for operation.

The software used by computer 16 is charted in FIGS. 2 through 12 with each of these figures representing a major component of the software.

Figure 2:
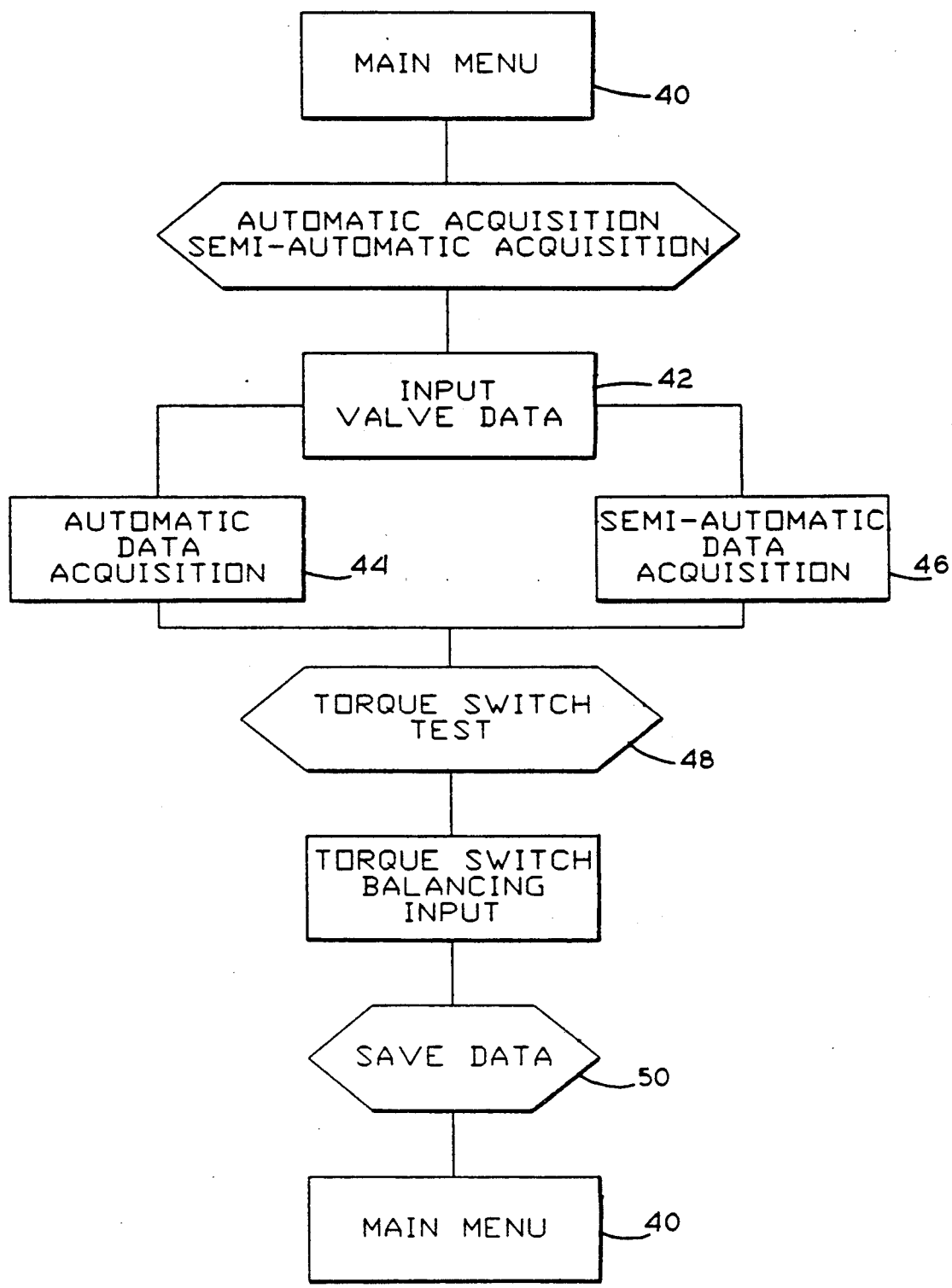
FIG. 2 is a partial flow diagram illustrating the Test Spring Pack component of the software program.

FIG. 2 pertains to the Test Spring Pack component of the software and it shows the basic path the program follows as the test progresses. This component of the software program allows the user to automatically or semi-automatically test spring pack 18 using testing assembly 10. Starting with Main Menu block 40, the user selects whether computer 16 will record data at preselected and pre-programmed points (automatic acquisition) or whether the computer will record data at points to be selected by the user (semi-automatic acquisition).

Automatic acquisition permits computer 16 to record force and displacement data automatically as spring pack 18 is manually compressed in test stand 12. Computer 16 is triggered on the displacement readings as measured by LVDT 36. When these displacement readings equal a specific pre-determined point, computer 16 automatically records the exact force applied at this displacement value. This automatic method enables a more accurate comparison of spring pack 18 to previous tests or to known standards.

Semi-automatic acquisition mode records data during the compression of spring pack 18 whenever the proper key is pressed. This option enables the user to record data at force or displacement points selected by the user during testing.

Input valve data block 42 provides a place, prior to testing, for recording unique valve operator information, spring pack information, force, and thrust limits. This information is used to evaluate spring pack 18 numerically as well as graphically.

Automatic data acquisition block 44 and semi-automatic data acquisition block 46 represent the point in the program where spring pack 18 is actually tested, depending on the option previously chosen. It is during these blocks 44 and 46 that (a) sensor calibration data is verified, (b) spring pack 18 is placed in test stand 12, (c) LVDT 36 is zeroed out, (d) load cell 28 is zeroed out, (e) the data according to the option selected (automatic or semi-automatic) is recorded, and (f) the final data point is taken by pressing the proper key.

Torque switch test block 48 allows the user the option of manually entering torque switch data that has been gathered from a torque switch balancing test. The torque switch balancing test is a separate test and in this embodiment, the data is manually entered. If the user chooses not to enter torque switch data, then block 48 is skipped.

Save data block 50 gives the user the option of saving the data from the test just performed or discarding this data. The program then returns the user to main menu 40.

Figure 3:
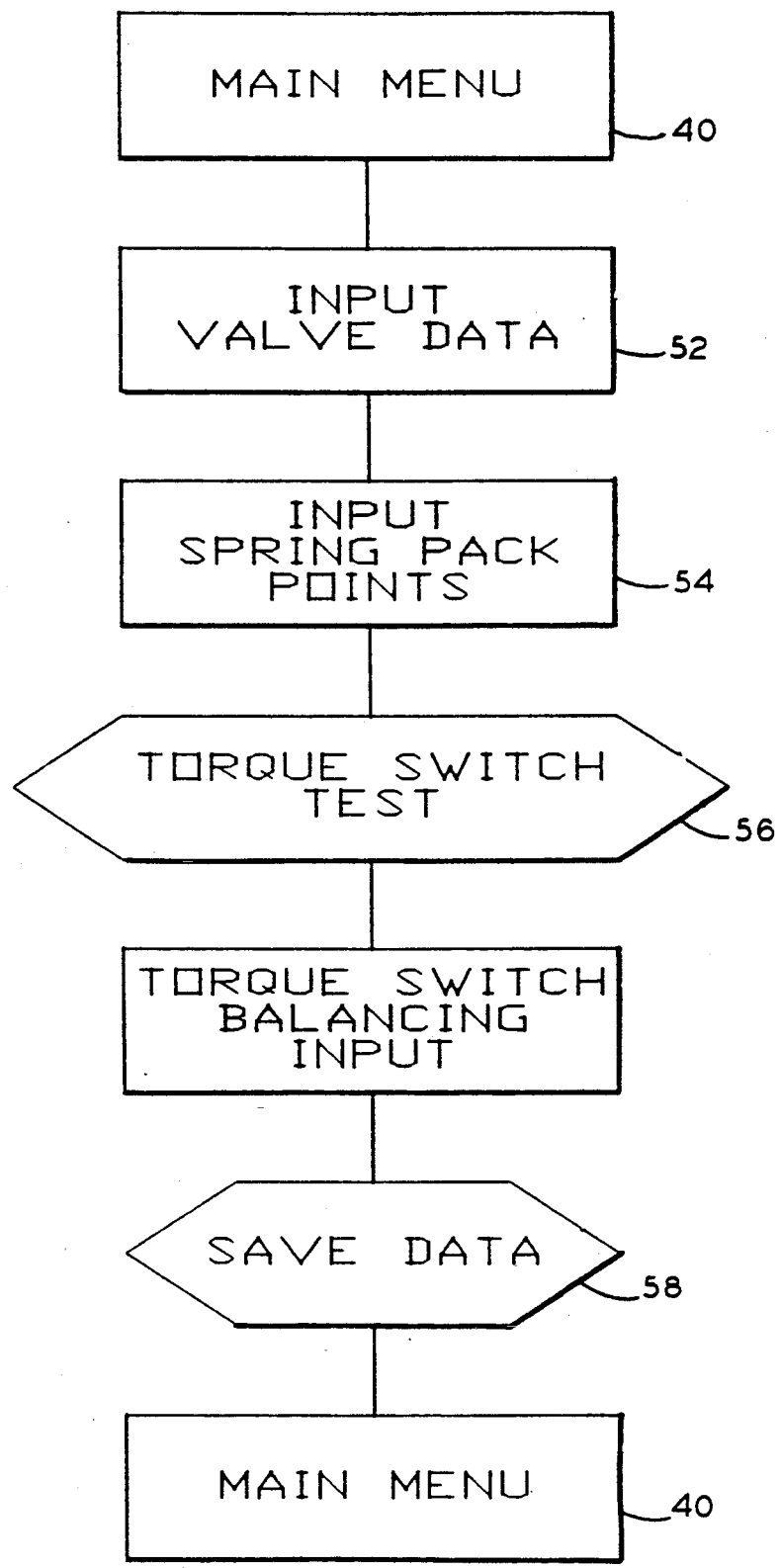
FIG. 3 is a partial flow diagram illustrating the Manual Input of Test Data component of the software program.

FIG. 3 pertains to the manual input of test data as compared with the automatic or semi-automatic input of such data as explained in FIG. 2. This manual component of the software allows the user to manually enter or modify spring pack data without using test stand 12. Following this selection on main menu 40, input valve data block 52 provides the user a place for recording unique valve operator information, spring pack information, force, and thrust limits. This information is used to evaluate spring pack 18 both numerically and graphically.

Input spring pack points block 54 provides the operator the option of entering spring pack data by hand or modifying existing data from a previous test. Torque switch test block 56 gives the user the option of inputting torque switch data that has been gathered from a separate torque switch balancing test. In this embodiment, the torque switch balancing test data is entered manually. Of course, if no such data is to be entered, this block 56 is skipped.

Save data block 58 gives the user the option of saving the data from the test just performed or discarding this data. The program then returns the user to main menu 40.

Figure 4:
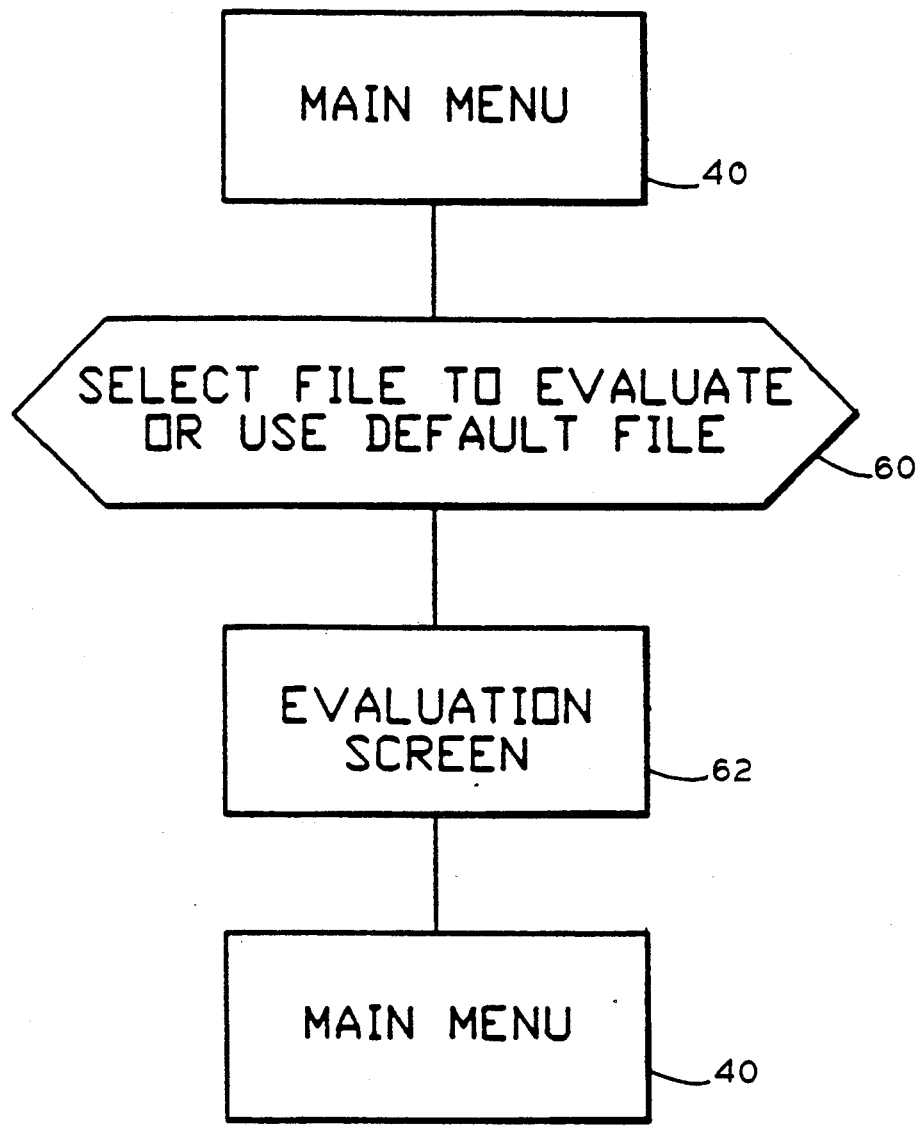
FIG. 4 is a partial flow diagram illustrating the Evaluation component of the software program.

FIG. 4 pertains to the evaluation portion of this software and it allows the user to numerically evaluate data gathered from the testing of spring pack 18, whether such data has been entered automatically, semi-automatically or manually. Again, starting from main menu block 40, the user is given the option in block 60 of selecting a test. In the case a spring pack test has already been performed, it will be evaluated automatically by computer 16 (default file) until another test is selected. Evaluation screen block 62 displays the test number and evaluates the test using the parameters entered as per either FIGS. 2 or 3. If the automatic or semi-automatic methods of FIG. 2 are used to evaluate the spring pack test, the parameters followed are lubricated thrust, non-lubricated thrust, approximate torque switch setting, and as-found values. The user has the ability to evaluate any spring pack test by using a pick list screen. Any information not entered during the test or out of calculation range is listed as "not calculated". Once this portion of the software is completed, the user is returned to main menu block 40.

Figure 5:
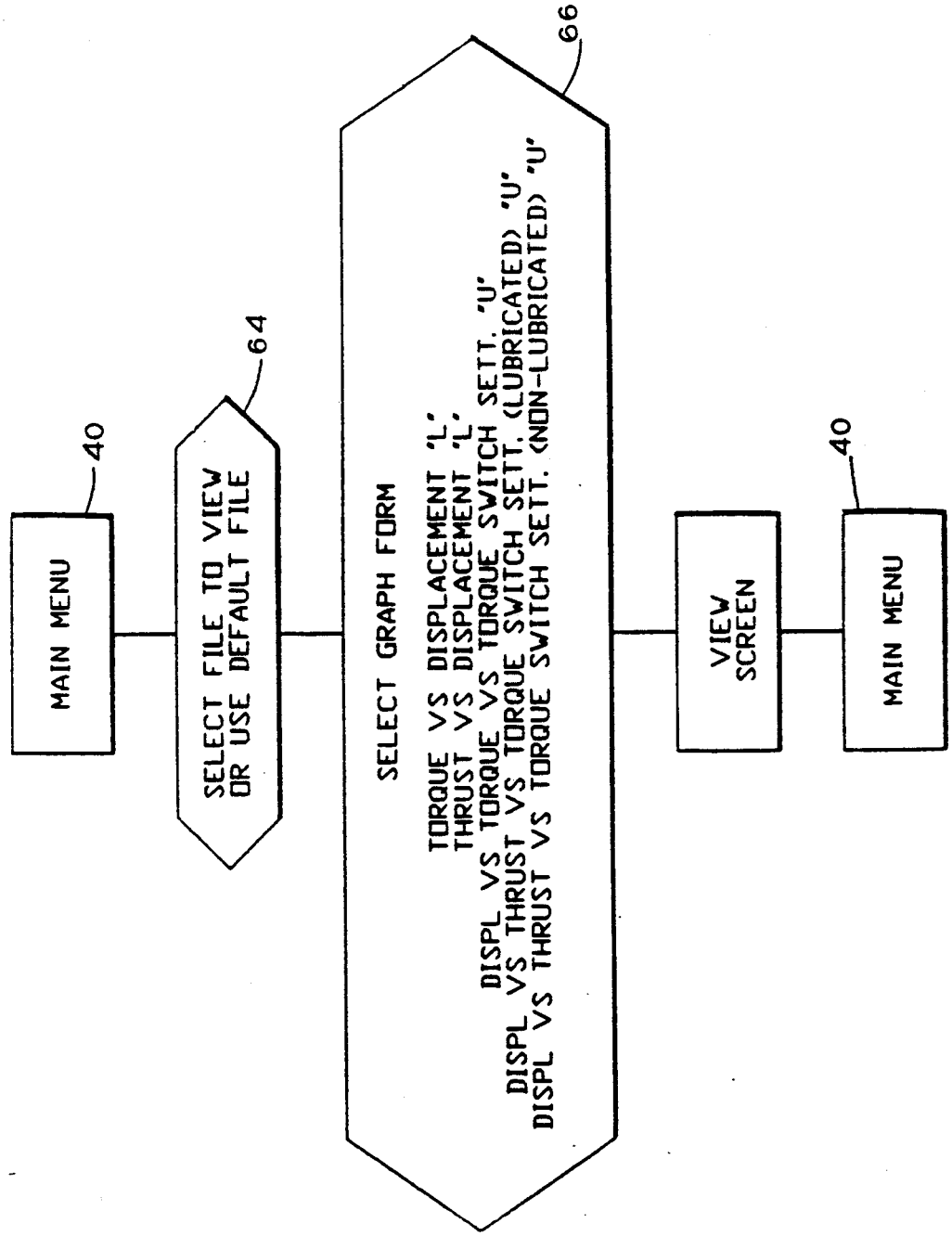
FIG. 5 is a partial flow diagram illustrating the Graphics component of the software program.

FIG. 5 pertains to the graphics portion of the software and it allows the user to view different graphs of the evaluated data. The user may print out the graph being viewed or the user may move a set of crosshairs to display an exact point's numerical values. Again, starting from main menu block 40, the user is allowed to select the test to be displayed as per select block 64. If a test has been previously performed, it is shown graphically by computer 16 (default value) until another test is selected.

Select graph form block 66 allows the user to select from five different graphs which will be subsequently displayed. These graphs are torque vs. displacement graph, thrust vs. displacement graph, displacement vs. torque vs. torque switch setting graph, displacement vs. thrust vs. torque switch setting (lubricated) graph, and displacement vs. thrust vs. torque switch setting (non-lubricated) graph. The user has the ability to view any selected graph of any test by using a pick list screen. Any information not entered during the spring pack test may prohibit the display of the graph chosen.

Figure 6:
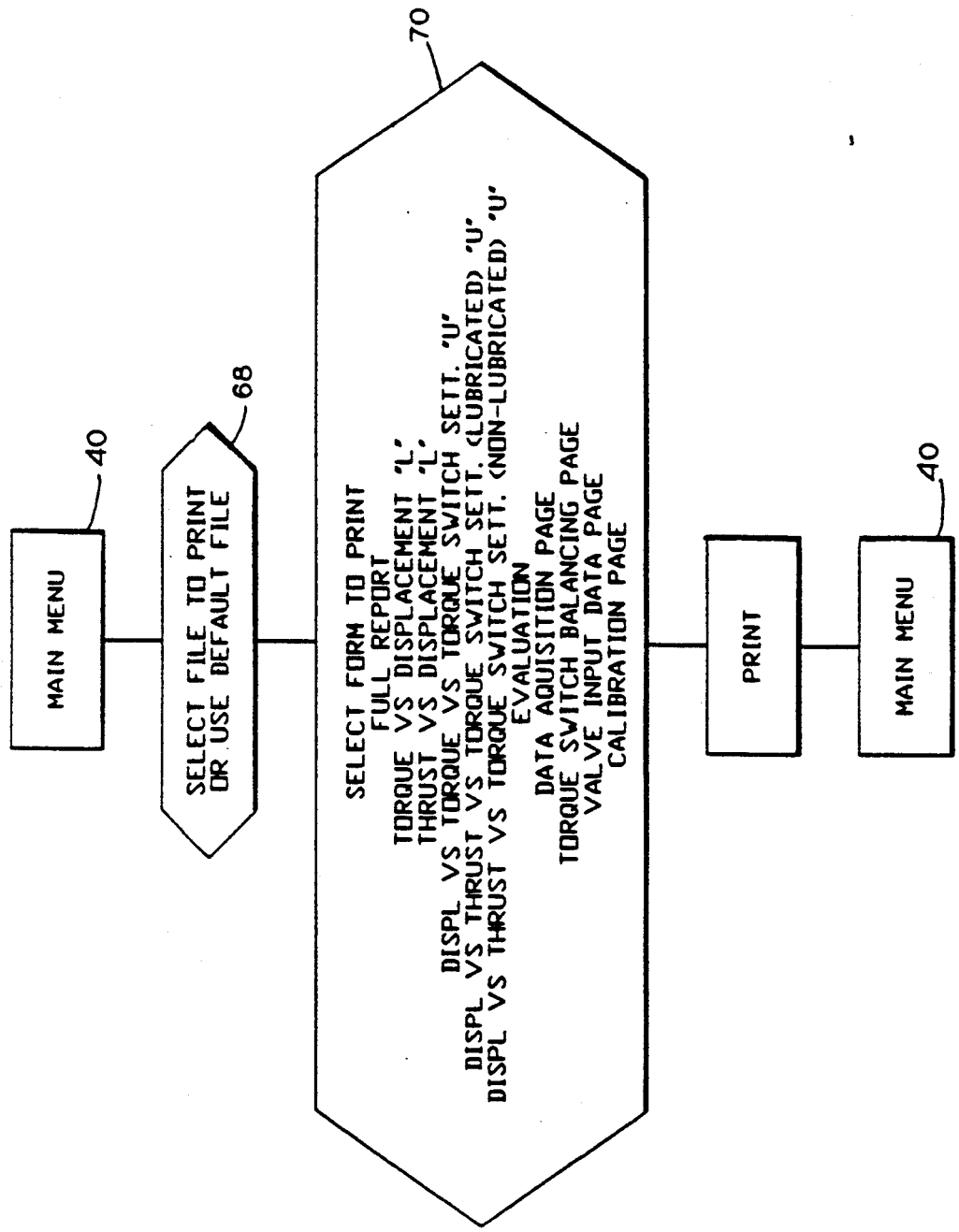
FIG. 6 is a partial flow diagram illustrating the Print Report component of the software program.

FIG. 6 pertains to the print report component of the software. It allows the user to print different tests, graphs, calibration information, and an evaluation page. Starting from main menu block 40, the user is given the option of selecting the test to be printed per select block 68. As before, if a test has previously been performed, it is defaulted to print by computer 16 until another test is selected.

Select form to print block 70 allows the user to select from among ten different printouts. These different print forms are full report, torque vs. displacement, thrust vs. displacement, displacement vs. torque vs. torque switch setting, displacement vs. thrust vs. torque switch setting (lubricated), displacement vs. thrust vs. torque switch setting (non-lubricated), evaluation page, data acquisition page, torque switch balancing page, valve input data page, and calibration page. If all of the above reports are desired, the user can select the "full report" option. The user has the ability to view any selected print of any test by using a pick list screen. Any information not entered during the spring pack test may prohibit the printing of the printout chosen.

Figure 7:
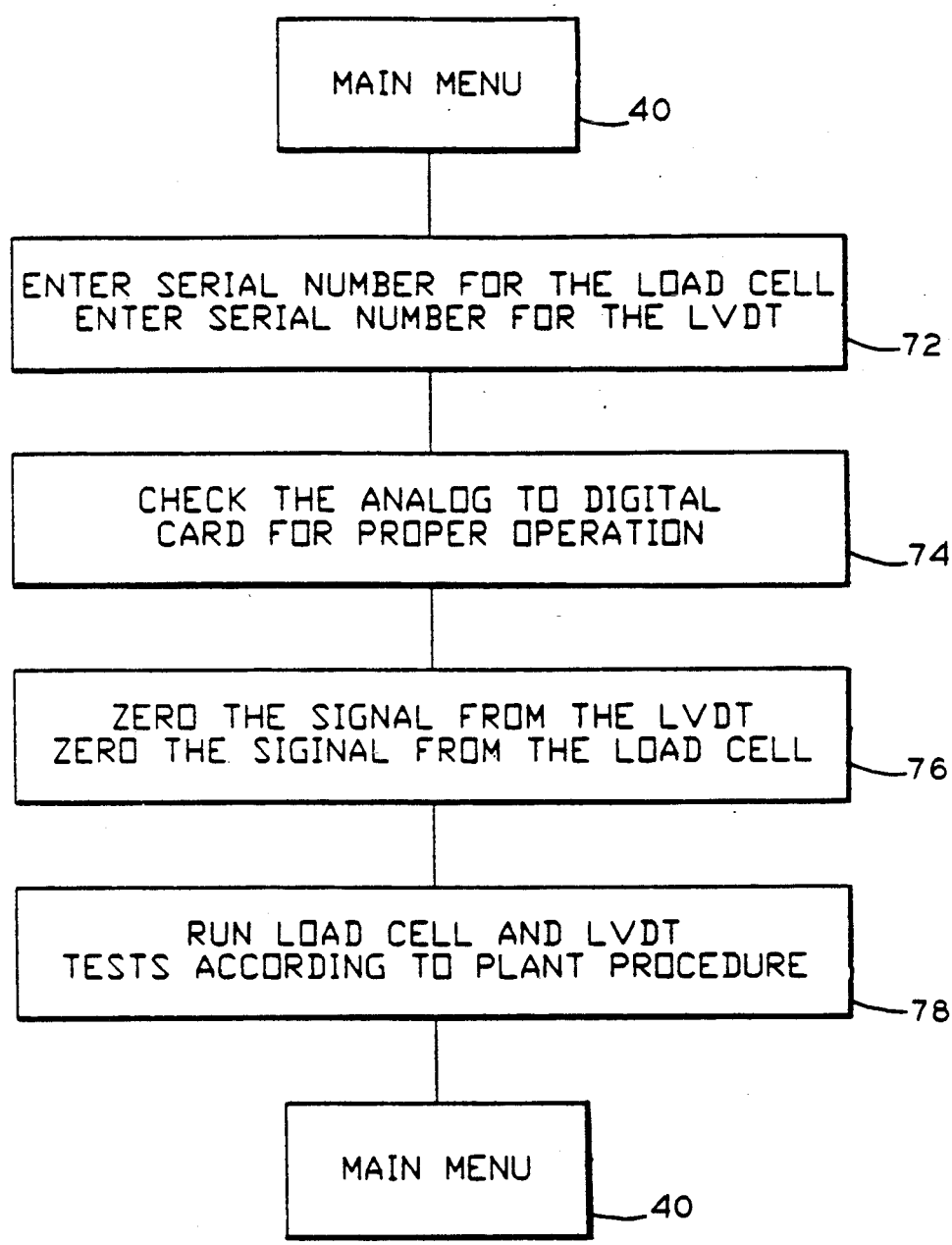
FIG. 7 is a partial flow diagram illustrating the Verify Calibration component of the software program.

FIG. 7 pertains to the verify calibration component of the software. It allows the user to test load cell 28 and LVDT 36 for accuracy. Enter serial number block 72 allows the user to enter this information about load cell 28 and LVDT 36. After this information is entered, computer 16 will be able to use the calibration information inputted as per FIG. 8. If the serial number is not entered or if the calibration of load cell 28 or LVDT 36 has expired, a warning message appears on the computer screen.

Check block 74 enables computer 16 to automatically check the analog to digital card for proper operation. Only if the card is not working or not installed will a warning message appear.

Zero signal block 76 and run block 78 allow the user to establish the zero point needed for proper testing. Test stand 12 is then adjusted according to plant procedure and the changes to load cell 28 and LVDT 36 are displayed on the computer screen. The plant procedures will dictate whether the sensors have passed the verification test.

Figure 8:
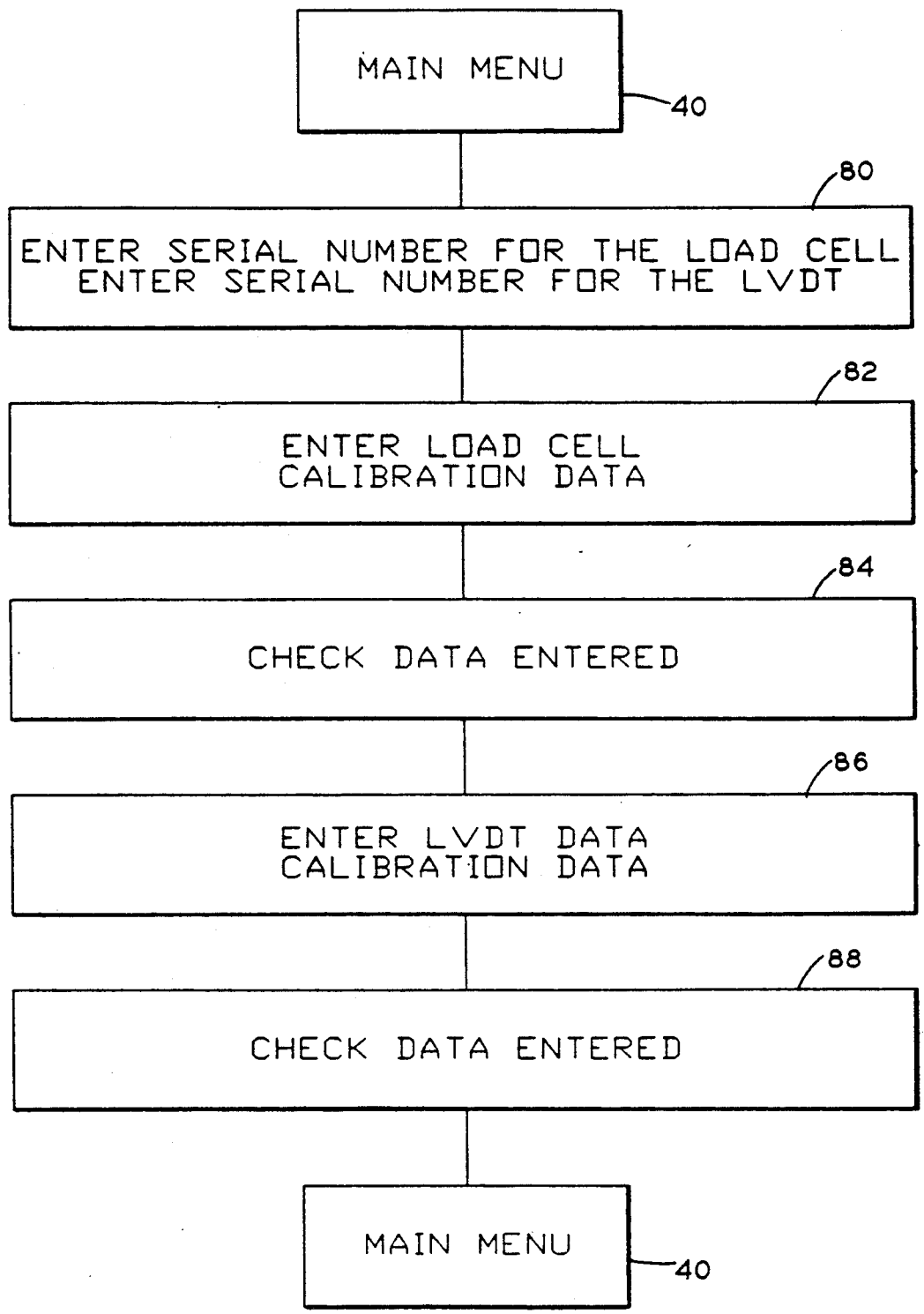
FIG. 8 is a partial flow diagram illustrating the Calibration Information component of the software program.

FIG. 8 pertains to the calibration information component of the software. It allows the user to enter calibration information for load cell 28 and LVDT 36. This information includes pounds per milli-volt for load cell 28 or inches per milli-volt for LVDT 36. The calibration expiration date is also entered for each sensor.

Enter serial number block 80 allows computer 16 to utilize the serial number of load cell 28 or LVDT 36 to create files for the calibration information entered. Enter load cell block 82 and check data block 84 allows the user to enter the calibration information for load cell 28. When the user exits this screen, computer 16 automatically checks the data entered for a numerical ascending sequence. If the calibration data is not in ascending order, a warning message will appear.

Enter LVDT data block 86 and check data block 88 allows the user to enter the calibration information for LVDT 36. When the user exits this screen, computer 16 automatically checks the data entered for a numerical ascending sequence. If the calibration data is not in ascending order, a warning message will appear.

FIG. 9 pertains to the pick another plant component of the software. It allows the user to select another plant or system to work with. Each plant or system has its own DOS subdirectory and in each subdirectory, different tests are associated with that plant or subdirectory. Select block 90 allows the user to select a plant name (or system) from a pick list or create a new one if such is desired. Once this is done, the spring pack software program will add new tests to this subdirectory or display any current tests in this subdirectory.

FIG. 10 pertains to the hardware setup component of the software. It allows the user to select the printer types available in the software and the communications mode. Also the analog to digital card's software address can be changed if necessary. The printer selection block 92 allows the user to select a different printer from a list and the preferred communications mode. If the user elects to change the analog to digital address, select block 94 permits this change in the software address of the card. The software address of the card must agree with the DIP settings on the analog to digital card.

Figure 11:
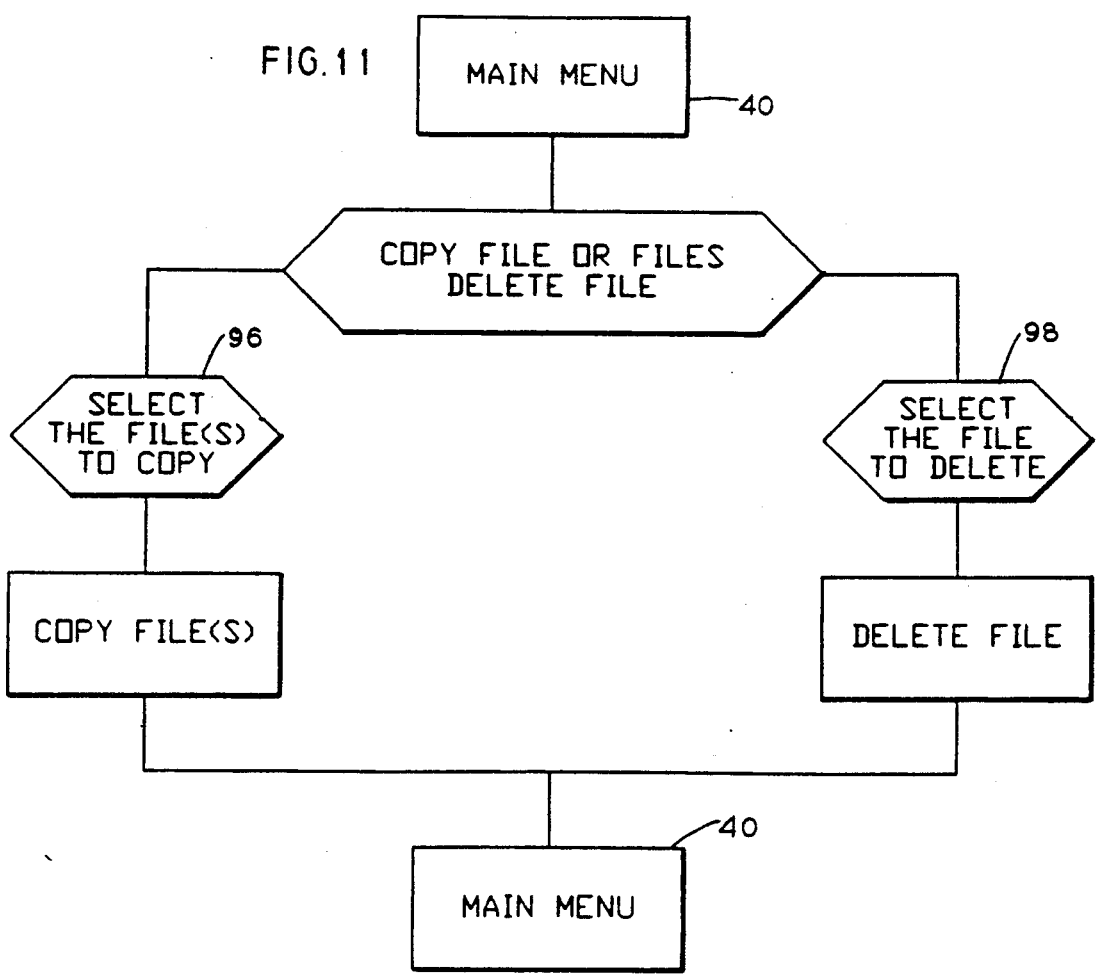
FIG. 11 is a partial flow diagram illustrating the File Utility component of the software program.

FIG. 11 pertains to the file utility component of the software. It allows the user to copy spring pack test files from one subdirectory to another or to a disk. Also, this component enables a spring pack test file to be deleted from any subdirectory.

If select the file(s) to copy block 96 is chosen, the user can copy test files from one subdirectory to another or to a disk. The user first selects one file (or all the files) in a subdirectory to copy and then selects what subdirectory or disk to copy the files to. A confirmation message appears if the process is successful.

If select the file to delete block 98 is chosen, the user can select a spring pack test file from a subdirectory and then delete it. A confirmation message appears if the deletion was successful.

Figure 12:
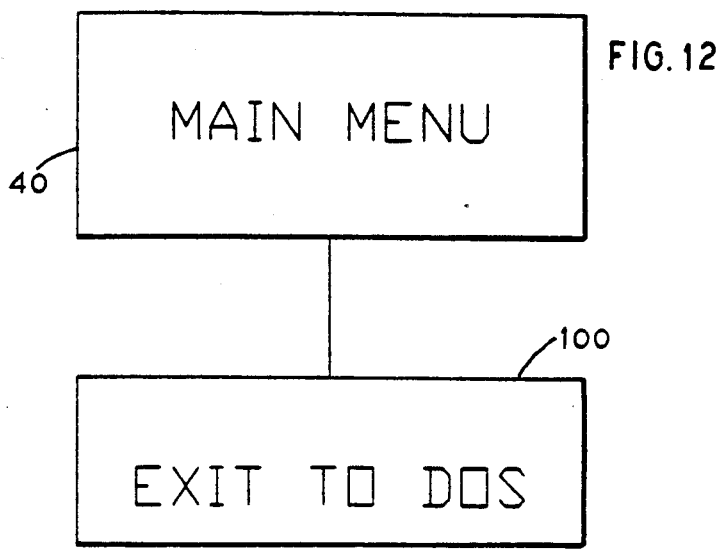
FIG. 12 is a partial flow diagram illustrating the Quit component of the software program.

FIG. 12 pertains to the quit component of the software. Exit to DOS box 100 allows a user to stop the program and return the user to a DOS prompt.

From the above, this invention provides a user friendly system for testing spring packs 18. It also provides an automatic means of collecting data from spring pack testing assembly 10. Under this automatic mode, the data collected enables accurate comparison of tests and repeatable tests to be made. This software also enables the separate torque switch balancing test data to be stored with the spring pack test data. Additionally, there are automatic filing methods for storing tests and automatic means for retrieving previous tests. This invention provides equations for evaluating and calculating proper torque switch test positions and it provides the ability to edit test data if erratic points were recorded. It can also save the new test data to a new test file thus avoiding having to alter the original data.

Other features of the software provide the ability to evaluate, view, and compare a spring pack test before saving the test file. It also enables the ability to graphically display valid test data in the form of "L" graphs (torque vs. displacement and thrust vs. displacement) and the ability to overlay spring pack standard curves or previous tests on the "L" graphs. Additionally, the software provides the ability to graphically display valid test data in the form of "U" graphs (the other three graphs discussed above). With this software, the user can select and view any test while viewing the "L" or the "U" graph above. Other functions include the ability to print the graph viewed to the selected printer or file and the ability to print to the selected printer or file the valve information page, test data pages, all graphs and calibration information. Finally, this software provides the ability of checking the entire system for accuracy according to a plants individual requirements and it provides more precise readings by interpolating the calibration information entered when using spring pack test stand 12.

What is claimed is:

1. A method of testing the spring pack of a motor operated valve comprising the steps of:
    a) compressing the spring pack in a test stand;
    b) continuously measuring the external compressive load applied to the spring pack;
    c) separately and continuously measuring the displacement of the spring pack due to the compressive load applied;
    d) electronically delivering said compressive load measurements and said displacement measurements to a computer;
    e) matching said delivered displacement measurements with preselected values thereof in said computer;
    f) recording a said compressive load measurement that corresponds to said pre-selected displacement value, said specific recording automatically occurring for three or more different said displacement values; and,
    g) reporting via said computer and for subsequent use, these said pre-selected displacement values and their respective said compressive load measurements.

2. The method as set forth in claim 1 wherein said pre-selected displacement values are selected by said computer.

3. The method as set forth in claim 1 wherein said pre-selected displacement values are selected by the user during the testing of the spring pack.

4. The method as set forth in claim 1 wherein said compressive load measurements are generated by a load cell and wherein said displacement measurements are generated by a linear variable differential transformer.

5. The method as set forth in claim 4 further comprising the step of verifying the calibration of said load cell and said linear variable differential transformer.

6. The method as set forth in claim 5 wherein said reporting comprises the computer generation of at least one graph contrasting the displacement of the spring pack with the compressive load applied.

7. The method as set forth in claim 6 wherein said compressive load applied is graphed as a function of either valve torque or valve thrust.

8. The method as set forth in claim 5 wherein said reporting comprises the computer generation of at least one report pertaining to the displacement of the spring pack with the compressive load applied.

9. The method as set forth in claim 8 wherein said report pertains to said compressive load measurements as a function of either valve torque or valve thrust.

* * * * *